US006407027B2

(12) United States Patent
Soloveichik et al.

(10) Patent No.: US 6,407,027 B2
(45) Date of Patent: Jun. 18, 2002

(54) CATALYST COMPOSITION AND METHOD FOR PRODUCING DIARYL CARBONATES, USING BISPHOSPHINES

(75) Inventors: Grigorii Lev Soloveichik, Latham; Ben Purushatom Patel, Albany; John Yaw Ofori, Niskayuna; Kirill Vladimirovich Shalyaev, Clifton Park, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/813,394

(22) Filed: Mar. 21, 2001

Related U.S. Application Data

(62) Division of application No. 09/466,031, filed on Dec. 20, 1999, now Pat. No. 6,245,929.

(51) Int. Cl.[7] .......................... B01J 31/00; B01J 27/06; B01J 23/00; B01J 23/58; B01J 23/44

(52) U.S. Cl. ...................... 502/150; 502/103; 502/104; 502/121; 502/130; 502/154; 502/155; 502/156; 502/162; 502/164; 502/172; 502/224; 502/229; 502/304; 502/324; 502/328; 502/330; 502/331; 502/333; 502/339

(58) Field of Search .................... 502/103, 104, 502/121, 130, 150, 154–156, 162, 164, 172, 224, 229, 328, 330, 304, 333, 339, 331, 324

(56) References Cited

U.S. PATENT DOCUMENTS

| 4,187,242 A | | 2/1980 | Chalk | 260/463 |
|---|---|---|---|---|
| 4,201,721 A | | 5/1980 | Hallgren | 260/463 |
| 4,629,804 A | * | 12/1986 | Grate et al. | 560/24 |
| 5,380,907 A | | 1/1995 | Mizukami et al. | 558/270 |
| 5,498,789 A | | 3/1996 | Takagi et al. | 558/270 |
| 5,739,352 A | * | 4/1998 | Barner et al. | 548/472 |
| 5,830,989 A | * | 11/1998 | Cooley et al. | 528/392 |
| 5,898,079 A | * | 4/1999 | Pressman et al. | 558/274 |
| 6,001,768 A | * | 12/1999 | Buysch et al. | 502/330 |
| 6,197,991 B1 | * | 3/2001 | Spivack et al. | 502/350 |
| 6,215,015 B1 | * | 4/2001 | Patel et al. | 558/274 |

FOREIGN PATENT DOCUMENTS

| EP | 736512 | * 10/1996 | ........... C07C/68/00 |
|---|---|---|---|
| GB | 2311777 | 10/1997 | |
| WO | WO 95 06025 | 3/1995 | |
| WO | WO 97 08123 | 3/1997 | |

OTHER PUBLICATIONS

International Search Report for International Application No. PCT/US 00/32868. Jun. 2001.

* cited by examiner

Primary Examiner—Mark L. Bell
Assistant Examiner—Patricia L. Hailey
(74) Attorney, Agent, or Firm—S. Bruce Brown; Noreen C. Johnson

(57) ABSTRACT

Hydroxyaromatic compounds such as phenol are carbonylated with oxygen and carbon monoxide in the presence of a catalyst system comprising a Group VIII metal, preferably palladium; at least one bromide or chloride salt, preferably sodium bromide or a tetraalkylammonium bromide; at least one organic bisphosphine such as 1,3-bis(diphenylphosphino)propane or 1,4-bis(diphenylphosphino)butane; and a compound of a metal other than a Group VIII metal having an atomic number of at least 44, preferably a lead bromophenoxide. There may also be present a polar organic liquid as a cosolvent.

28 Claims, No Drawings

CATALYST COMPOSITION AND METHOD FOR PRODUCING DIARYL CARBONATES, USING BISPHOSPHINES

This application is a division of application Ser. No. 09/466,031, filed Dec. 20, 1999, now U.S. Pat. No. 6,245,929 which is hereby incorporated by reference in its entirety.

BACKGROUND OF THE INVENTION

This invention relates to the preparation of diaryl carbonates by carbonylation. More particularly, it relates to the improvement of diaryl carbonate yield in the carbonylation reaction.

Diaryl carbonates are valuable intermediates for the preparation of polycarbonates by transesterification with bisphenols in the melt. This method of polycarbonate preparation has environmental advantages over methods that employ phosgene, a toxic gas, as a reagent and environmentally detrimental chlorinated aliphatic hydrocarbons such as methylene chloride as solvents.

Various methods for the preparation of diaryl carbonates by an oxidative carbonylation (hereinafter sometimes simply "carbonylation" for brevity) reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is a heavy Group VIII metal; i.e., a Group VIII metal having an atomic number of at least 44, said metals consisting of ruthenium, rhodium, palladium, osmium, iridium and platinum, or a complex thereof. Palladium catalysts have been found particularly useful; they include complexes with phosphines such as triphenylphosphine.

The production of carbonates may frequently be improved by including a metal-based cocatalyst along with the heavy Group VIII metal catalyst. Metal-based cocatalysts have been described broadly in U.S. Pat. Nos. 4,187,242, 4,201,721 and 5,380,907. Lead compounds as cocatalysts are particularly detailed in U.S. Pat. No. 5,498,789. Also preferred in general is the use of various halides, as illustrated by tetra-n-butylammonium bromide. Compounds characterized as inert solvents, such as toluene, diethyl ether, diphenyl ether and acetonitrile, can also be present.

Many of the catalyst systems known in the art have disadvantages such as low active catalyst lifetime, typically 2 hours or less, and low selectivity to the desired diaryl carbonate as a result of formation of relatively high proportions of by-products such as bromophenols.

Also, it has been observed that certain palladium-based catalysts, such as palladium(II) acetate, show a decrease in catalytic activity upon storage in contact with hydroxyaromatic compounds such as phenol at temperatures on the order of 70° C. for periods as short as 2 hours. This decrease is notable particularly when the palladium compound is present in catalyst mixtures containing lead(II) oxide.

It is of interest, therefore, to develop catalyst systems that have long lifetimes, not decreased by storage, and which improve selectivity.

SUMMARY OF THE INVENTION

The present invention is based on the discovery that the presence of bisphosphines in carbonylation catalyst systems, whether added separately or as a preformed complex with the Group VIII metal, affords a catalyst with good activity and relatively long storage stability.

In one of its aspects, therefore, the invention is directed to a method for preparing a diaryl carbonate. An embodiment of the method comprises contacting at least one hydroxyaromatic compound with oxygen and carbon monoxide in the presence of a catalytic amount of a catalyst composition comprising at least one organic bisphosphine and the following optional components and any reaction products thereof: a Group VIII metal having an atomic number of at least 44 or a compound thereof; at least one bromide or chloride salt; and at least one cocatalyst which is a compound of a metal other than a Group VIII metal having an atomic number of at least 44.

Another aspect of the invention is catalyst compositions comprising the aforementioned components and any reaction products thereof.

DETAILED DESCRIPTION OF PREFERRED EMBODIMENTS

Any hydroxyaromatic compound may be employed in the method of the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl) propane or "bisphenol A", whereupon the products are polycarbonate oligomers.

Other reagents in the diaryl carbonate preparation method of the invention are oxygen and carbon monoxide, which react with the phenol to form the desired diaryl carbonate. They may be employed in high purity form or diluted with another gas such as nitrogen, argon or carbon dioxide, which has no negative effect on the reaction.

For the sake of brevity, the constituents of the catalyst system of the invention are defined as "components" irrespective of whether a reaction between said constituents occurs before or during the carbonylation reaction. Thus, the catalyst system may include said components and any reaction products thereof.

Component A of the catalyst system is one of the heavy Group VIII metals, preferably palladium, or a compound thereof. Thus, useful palladium materials include elemental palladium-containing entities such as palladium black, palladium/carbon, palladium/alumina and palladium/silica; palladium compounds such as palladium chloride, palladium bromide, palladium iodide, palladium sulfate, palladium nitrate, palladium acetate and palladium 2,4-pentanedionate; and palladium-containing complexes involving such compounds as carbon monoxide, amines, nitrites, phosphines and olefins. Preferred in many instances are palladium(II) salts of organic acids, most often $C_{2-6}$ aliphatic carboxylic acids, and palladium(II) salts of β-diketones. Palladium(II) acetate and palladium(II) 2,4-pentanedionate are generally most preferred. Mixtures of the aforementioned palladium materials are also contemplated.

Component B is at least one bromide or chloride salt. It may be an alkali metal or alkaline earth metal halide, preferably a bromide such as lithium bromide, sodium bromide, potassium bromide, calcium bromide or magnesium bromide. It may also be a quaternary ammonium or quaternary phosphonium salt such as tetramethylammonium bromide, tetraethylammonium bromide, tetra-n-butylammonium bromide or tetramethylphosphonium bromide, or a hexaalkylguanidinium salt such as hexaethylguanidinium bromide.

Component C is at least one organic bisphosphine. By "organic" is meant a compound containing at least one organic radical, with the proviso that said compound may also contain non-organic atoms or radicals. Thus, the bisphosphine may often be characterized by the formula $$(R^1)_2P-R^2-P(R^1)_2, \quad (I)$$

wherein each $R^1$ is independently a monovalent organic radical and $R^2$ is a divalent organic radical. Most often, $R^1$ is an aromatic or alicyclic radical, preferably aromatic and most preferably phenyl.

The identity of the divalent $R^2$ radical is subject to wide variation. It may be aliphatic, as exemplified by ethylene, trimethylene, tetramethylene and neopentylene. It may also be aromatic, as illustrated by phenylene and naphthylene. Suitable radicals include those containing inorganic elements, as illustrated by aminobis(alkylene) and ferrocenylene. For the most part, aliphatic radicals are preferred and $C_{3-8}$ aliphatic radicals especially preferred.

Many bisphosphines of formula I, particularly the ones in which $R^2$ is aliphatic, are commercially available; examples are 1,3-bis(diphenylphosphino)propane and 1,4-bis(diphenylphosphino)butane. Other bisphosphines can be prepared by art-recognized methods.

Bisphosphines are included in the carbonylation catalyst system in catalytic amounts. In this context a "catalytic amount" is an amount of bisphosphine (or combination of bisphosphines) that increases the number of moles of diaryl carbonate produced per mole of Group VIII metal utilized; increases the number of moles of diaryl carbonate produced per mole of halide utilized; or increases selectivity toward diaryl carbonate production beyond that obtained in the absence of the bisphosphine (or combination of bisphosphines). Optimum amounts of a bisphosphine in a given application will depend on various factors, such as the identity of reactants and reaction conditions.

It is within the scope of the invention to introduce component C, the bisphosphine, into the catalyst mixture as a discrete compound. It is also contemplated to preform a complex of the bisphosphine with the Group VIII metal of component A, whereupon components A and C are introduced as a single entity. This may be achieved, for example, by a ligand interchange reaction between the bisphosphine and a palladium(II) halide complex with another ligand such as acetonitrile.

The preparation of a palladium(II) bisphosphine complex is illustrated by the following example.

EXAMPLE 1

A 100-ml round-bottomed flask was charged with 484.0 mg (1.87 mmol) of commercial grade palladium(II) chloride-acetonitrile complex and 30 ml of acetonitrile. The resulting solution was heated to about 40° C. with vigorous stirring until the palladium salt completely dissolved; a bright orange homogeneous solution resulted. To the stirred solution was added, in one portion, 797.0 mg (1.87 mmol) of 1,4-bis(diphenylphosphino)butane. The phosphine readily dissolved, and a pale yellow precipitate formed instantly. The suspension thus formed was stirred for an additional 5 minutes at room temperature and then cooled in an ice bath for 30 minutes to complete precipitation. The pale yellow precipitate was filtered in air on a medium pore fritted glass filter and washed with reagent grade hexane. It was then dried under vacuum. The yield of the desired palladium(II) chloride bisphosphine complex, whose structure was confirmed by phosphorus-31 nuclear magnetic resonance spectroscopy, was 1.062 g, or 94% of theoretical.

Also present in the catalyst composition is (D) at least one cocatalyst which is a compound of a metal other than a heavy Group VIII metal, preferably one which is soluble in the liquid phase under the reaction conditions. Numerous other metal compounds are known in the art to be active as carbonylation cocatalysts, and any compound having such activity may be used according to the present invention provided an improvement in diphenyl carbonate production, usually yield, is achieved thereby.

Illustrative cocatalytic metals include cerium, titanium, copper, zinc, manganese, bismuth, europium and lead, which may be used singly or in combination. It should be noted, however, that not all possible permutations of component D are operative in all contexts; the effectiveness of any metal compound or combination of compounds for this purpose may be determined by simple experimentation. The preferred cocatalytic compounds are those of lead.

Examples of lead compounds which may be employed are lead oxides such as PbO and $Pb_3O_4$; inorganic lead salts such as lead(II) nitrate; lead carboxylates such as lead(II) acetate, lead(II)propionate and lead(IV) acetate; lead alkoxides and aryloxides such as lead(II) methoxide and lead(II) phenoxide; and lead salts of β-diketones such as lead(II) 2,4-pentanedionate. Mixtures of the aforementioned lead compounds may also be employed. The preferred lead compounds are lead(II) oxide, lead(II) aryloxides and lead (II) 2,4-pentanedionate. The preferred compounds of other metals are, for the most part, salts of β-diketones and especially 2,4-pentanedionates.

A subgenus of lead cocatalytic compounds that are particularly useful according to the invention is the subgenus of lead halophenoxides, typically having the formula $$Pb_nO_m(OA)_{(2-z)(n-m)}X_{z(n-m)}, \quad (II)$$

wherein A is an aromatic radical, X is chlorine or bromine, n has a value in the range of 1–3, m has a value in the range of 0–1 and z has a value in the range of 0.1–2.0.

In formula II, A may be any aromatic radical, unsubstituted or substituted. In general, A corresponds to the diaryl carbonate to be formed in the carbonylation reaction. Therefore, it is usually unsubstituted phenyl. X may be bromide or chloride and is preferably bromide.

The values of n, m and z are as described hereinabove. Most often, n is 2.5–3 and m is 0.8–1.

The lead halophenoxides may be prepared by merely bringing into contact, usually at a temperature in the range of about 50–120° C., lead(II) oxide, at least one bromide or chloride salt and at least one hydroxyaromatic compound, most often phenol. Suitable bromide and chloride salts include alkali metal and alkaline earth metal bromides and chlorides and tetraalkylammonium, tetraalkylphosphonium and hexaalkylguanidinium bromides and chlorides. The bromides are strongly preferred. When the bromide or chloride salt is an inorganic salt such as sodium bromide, the reaction is preferably facilitated by the presence of an electron-donating compound, especially a nitrile such as acetonitrile.

The molar ratio of lead to halide in the reaction mixture should be at least 2:1, since at lower molar ratios the principal products are the lead(II) halides and hydroxyhalides. In general, molar ratios in the range of about 2–20:1 are preferred. It should be noted, however, that the molar ratio of lead to halide in the product is not necessarily at least 2:1. Rather, the method of the invention involves this minimum since it permits isolation of the lead halophenoxide.

Hydroxyaromatic compound is most often present in excess and is preferably employed as a solvent for the reaction. The electron-donating compound, when employed, may also be present in molar excess with respect to halide salt, typically in a molar ratio in the range of about 50–200:1. Under such conditions, the lead halophenoxide forms a separate phase, which may be isolated by conventional methods including such operations as filtration and drying.

The preparation of lead halophenoxides is illustrated by the following, non-limiting Examples.

EXAMPLES 2–7

Various proportions of tetra-n-butylammonium bromide (TBAB) or hexaethylguanidinium bromide (HEGB) and phenol (PhOH) were combined with lead(II) oxide (PbO) and the resulting mixtures were stirred overnight at 70° C. After cooling to room temperature, the solid precipitates were removed by filtration, washed twice with acetonitrile and dried in a vacuum oven at 100° C.

EXAMPLES 8–9

Lead(II) oxide (PbO), 2.715 g, was dissolved in 10 ml of phenol (PhOH) at 100° C. and the resulting solution was added to various amounts of sodium bromide suspended in a mixture of 5 ml of phenol and 5 ml of acetonitrile (ACN). The resulting mixtures were stirred overnight at 100° C. After cooling to room temperature, the solid precipitates, which were the desired lead bromophenoxides, were removed by filtration, washed twice with acetonitrile and dried in a vacuum oven at 100° C.

The proportions and analyses applicable to the products of Examples 2–9 are given in Table I.

Component A is most often present in the amount of about 0.1–10,000 ppm by weight of the appropriate Group VIII metal (usually palladium), based on hydroxyaromatic compound, and component B in the amount of about 1–2,000 equivalents of halide per equivalent of the Group VIII metal of component A. Component C is present in an amount effective to form a complex with the metal of component A; this amount is generally at least a number of moles equal to the number of gram-atoms of metal in said component A, and preferably in a ratio of moles of component C to gram-atoms of said metal in the range of about 1.0–1.2:1. Component D, when present, is generally employed in the amount of about 0.2–200 gram-atoms of total metal per equivalent of the Group VIII metal of component A.

The role of component E in the composition and method of the invention is believed to be to increase the degree of dissociation and ionization of the halide anion of component B, perhaps by forming a complex with the cationic portion of said component, although the invention is in no way dependent on this or any other theory of operation. The amount of component E employed will be an amount effective to increase the yield of the desired diaryl carbonate as evidenced, for example, by an increase in "turnover number"; i.e., the number of moles of diaryl carbonate formed per gram-atom of palladium present. This amount is most often about 1–60% by volume based on the total of hydroxyaromatic compound and component E.

The method of the invention is preferably conducted in a reactor in which the hydroxyaromatic compound and catalyst system are charged under pressure of carbon monoxide

TABLE I

| Example | 2 | 3 | 4 | 5 | 6 | 7 | 8 | 9 |
|---|---|---|---|---|---|---|---|---|
| Bromide: | | | | | | | | |
| Identity | TBAB | TBAB | HEGB | HEGB | HEGB | HEGB | NaBr | NaBr |
| Amount, mg | 570 | 2,850 | 540 | 510 | 570 | 155 | 150 | 75 |
| PbO, mg | 1,000 | 5,030 | 1,000 | 1,800 | 2,500 | 1,800 | 2,700 | 2,700 |
| Molar ratio, Pb/Br | 2.5 | 2.55 | 2.55 | 4.4 | 6.8 | 16.0 | 8.3 | 16.6 |
| Solvent: | | | | | | | | |
| Identity | PhOH | PhOH | PhOH | PhOH | PhOH | PhOH | PhOH/ACN | PhOH/ACN |
| Amount, ml | 10 | 50 | 10 | 10 | 10 | 10 | 20 | 20 |
| Yield, %* | 62.0 | 44.0 | 65.7 | 68.0 | 49.7 | 38.8 | 36.1 | 87.8 |
| Br, % | 8.0 | 8.8 | 8.3 | 5.2 | 5.4 | 2.1 | 6.3 | 1.4 |
| Pb, % | 62.9 | 61.8 | 63.5 | 62.0 | 60.9 | 58.7 | 60.3 | 58.6 |

*Based on PbO.

The presence of (E) a cosolvent in the catalyst system is also often preferred. Suitable cosolvents include various polar organic liquids such as ethers including polyethylene glycol ethers, amides such as N-methylpyrrolidinone, sulfones such as sulfolane and nitriles such as acetonitrile and adiponitrile. It should be noted, however, that component E is not effective to optimize diaryl carbonate formation for all possible permutations of component D; the combined effectiveness of the two for this purpose may be determined by simple experimentation.

In addition to the aforementioned reactants and catalyst system, it is strongly preferred for a desiccant to be present in the reaction system. The preferred desiccants are nonreactive materials such as molecular sieves, as illustrated by 3-Ångstrom (hereinafter "3A") molecular sieves. They are usually isolated from the other reactants, as by presence in a basket mounted to a stirrer shaft or the like.

and oxygen and heated. The reaction pressure is most often within the range of about 1–500 and preferably about 1–150 atm. Gas is usually supplied in proportions of about 1–50 mole percent oxygen with the balance being carbon monoxide and optionally one or more inert gases, and in any event outside the explosion range for safety reasons. The gases may be introduced separately or as a mixture. Reaction temperatures in the range of about 60–150° C. are typical. It is often preferred to maintain a substantially constant gas pressure and partial pressure of carbon monoxide and oxygen, as described, for example, in U.S. Pat. No. 5,399,734, until conversion of the hydroxyaromatic compound is complete.

The diaryl carbonates produced by the method of the invention may be isolated by conventional techniques. It is often preferred to form and thermally crack an adduct of the diaryl carbonate with the hydroxyaromatic compound, as described in U.S. Pat. Nos. 5,239,106 and 5,312,955.

The method of the invention is illustrated by the following examples. Minor variations in reagent amounts from one example to another are not believed significant from the standpoint of yield.

EXAMPLES 10–14

In each experiment, a high pressure reactor equipped with a stirrer was charged with approximately 61.318 g (651 mmol) of phenol, 301 mg of the lead bromophenoxide of Example 3, 1,750 mg (8.32 mmol) of tetraethylammonium bromide and a preformed mixture of 4.8 mg (0.016 mmol) of palladium(II) 2,4-pentanedionate and 0.016 mmol of one of the following bisphosphines:

DPPP- 1,3-bis(diphenylphosphino)propane,
DPPB-1,4-bis(diphenylphosphino)butane,
DPPF-bis(diphenylphosphino)ferrocene,
DCPF-bis(dicyclohexylphosphino)ferrocene,
DPAP-bis(diphenylphosphino)propylamine.

Freshly activated Type 3A molecular sieves, 38 g, were placed in a perforated polytetrafluoroethylene basket mounted on the stirrer shaft.

The reactor was sealed, flushed twice with carbon monoxide, pressurized with 88.4 atmospheres of a carbon monoxide-oxygen mixture containing 7.5% oxygen by volume and heated for 5 hours at 100° C., with vigorous stirring and periodic sampling via a sample dip tube.

When the reaction was complete, the reactor contents were cooled and analyzed. The results are given in Table II, as averages of quadruplicate runs. "Turnover number" is the number of moles of diaryl carbonate formed per gram-atom of palladium present, and "selectivity" (to diphenyl carbonate) is the amount of diphenyl carbonate produced as a percentage of total reaction products derived from phenol. Comparison is made with a control in which no bisphosphine was employed.

TABLE II

| Example | Bisphosphine | Turnover number | Selectivity, % |
|---|---|---|---|
| 10 | DPPP | 6,075 | 77.0 |
| 11 | DPPB | 5,260 | 82.3 |
| 12 | DPPF | 4,490 | 61.4 |
| 13 | DCPF | 4,690 | 56.0 |
| 14 | DPAP | 6,040 | 65.8 |
| Control | — | 4,340 | 67.2 |

As demonstrated in Table II, the turnover numbers in the examples are higher than that of the control. In particular, excellent turnover numbers are produced by the bisphosphines in which $R^2$ is aliphatic. Certain compositions of the invention (Examples 10 and 11) also afford higher selectivities than the control.

EXAMPLES 15–20

Carbonylation experiments were conducted in small vials, employing a catalyst system containing 12 equivalents of lead(II) oxide, 5.6 equivalents of cerium(III) 2,4-pentanedionate and 400 equivalents of tetraethylammonium bromide per equivalent of palladium. The palladium catalysts were stored for various periods before use, and the reaction mixtures in various examples were stored at 70° C. for various periods. The proportion of palladium was 0.25 mmol per mmol of phenol and the reaction volume was 25 $\mu$l.

Each vial was capped with a snap cap having a slit with a polytetrafluoroethylene septum and the vials were placed in an autoclave which was pressurized to 88.4 atm with a mixture of 90 mole percent carbon monoxide and 10 mole percent oxygen and heated at 100° C. for 3 hours. The contents of the vials were analyzed for diphenyl carbonate by vapor phase chromatography. The results are given in Table III, in comparison with controls employing palladium (II) 2,4-pentanedionate as a catalyst.

TABLE III

| Example | Catalyst storage, hrs. | Heated mixture storage, hrs. | Turnover number | Turnover number, control |
|---|---|---|---|---|
| 15 | 4 | 4 | 1,926 | 801 |
| 16 | 4 | 2 | 2,036 | 891 |
| 17 | 4 | 0 | 2,132 | 2,510 |
| 18 | 2 | 2 | 2,000 | 841 |
| 19 | 2 | 0 | 1,879 | 2,330 |
| 20 | 0 | 0 | 2,018 | 2,368 |

It can be seen that the palladium(II) 2,4-pentanedionate catalyst systems show a very significant decrease in turnover number upon storage of the reaction mixture, although storage of the catalyst itself has no significant effect (compare Examples 17, 19 and 20). By contrast, the turnover numbers resulting from use of the catalyst systems of the present invention remain comparable under the same conditions.

The same pattern was not observed in catalyst systems not containing lead and cerium but containing copper(II) 2,4-pentanedionate, a homogeneous catalyst constituent. Turnover numbers of the same order of magnitude were observed irrespective of catalyst storage and reaction mixture storage for periods up to 20 and 4 hours, respectively.

EXAMPLES 21–53

Carbonylation experiments were conducted in small vials as described in Examples 15–20, employing the palladium (II) chloride bisphosphine complex of Example 1; sodium bromide (NaBr), calcium bromide ($CaBr_2$) or tri-n-butylammonium bromide (TBAB); and various cosolvents at levels of 24 ppm of palladium based on phenol, 240 equivalents of bromide per equivalent of palladium and 35% cosolvent by volume based on phenol-cosolvent mixture. Various cocatalyst compounds which included lead(II) oxide, titanium(IV) oxide bis(2,4-pentanedionate), zinc 2,4-pentanedionate, copper(II) 2,4-pentanedionate, cerium(III) 2,4-pentanedionate, iron(III) 2,4-pentanedionate, manganese(III) 2,4-pentanedionate, europium(III) 2,4-pentanedionate and bismuth(III) 2,2,6,6-tetramethyl-3,5-heptanedionate, alone or in combination, were employed as component E. The cosolvents employed were N-methylpyrrolidinone (NMP), tetraethylene glycol dimethyl ether ("tetraglyme" TEG), polyethylene glycol dimethyl ether (PEG), sulfolane (SULF) and adiponitrile (ACN) .The gas mixture consisted of 91.7 mole percent carbon monoxide and 8.3 mole percent oxygen.

The results are given in Table IV, as averages for triplicate runs. Cocatalyst proportions are in equivalents per equivalent of palladium. Comparison is made with controls in which no cosolvent was used and the proportion of phenol was increased correspondingly.

TABLE IV

| Example | Cocatalyst (eq) | Halide | Cosolvent | Turnover number | Turnover number, control |
|---|---|---|---|---|---|
| 21 | Cu(20) | NaBr | NMP | 713 | 222 |
| 22 | Cu(20) | NaBr | TEG | 1,023 | 222 |
| 23 | Cu(20) | NaBr | PEG | 1,065 | 222 |
| 24 | Cu(20) | NaBr | SULF | 588 | 222 |
| 25 | Ti(10), Zn(20) | NaBr | NMP | 697 | 158 |
| 26 | Ti(10), Zn(20) | NaBr | TEG | 483 | 158 |
| 27 | Ti(10), Zn(20) | NaBr | PEG | 429 | 158 |
| 28 | Ti(10), Zn(20) | NaBr | SULF | 735 | 158 |
| 29 | Ti(10), Zn(20) | NaBr | ACN | 600 | 158 |
| 30 | Pb(24), Ce(10) | NaBr | NMP | 1,342 | 665 |
| 31 | Pb(24), Ce(10) | NaBr | TEG | 1,456 | 665 |
| 32 | Pb(24), Ce(10) | NaBr | PEG | 1,318 | 665 |
| 33 | Pb(24), Ce(10) | NaBr | SULF | 1,058 | 665 |
| 34 | Pb(24), Ce(10) | NaBr | ACN | 1,111 | 665 |
| 35 | Pb(24), Ti(5.6) | NaBr | NMP | 1,373 | 547 |
| 36 | Pb(24), Ti(5.6) | NaBr | TEG | 1,321 | 547 |
| 37 | Pb(24), Ti(5.6) | NaBr | PEG | 613 | 547 |
| 38 | Pb(24), Ti(5.6) | NaBr | SULF | 962 | 547 |
| 39 | Pb(24), Ti(5.6) | NaBr | ACN | 835 | 547 |
| 40 | Pb(24), Ce(10) | CaBr$_2$ | TEG | 485 | 183 |
| 41 | Cu(10), Fe(10) | NaBr | PEG | 88 | 40 |
| 42 | Cu(10), Mn(10) | NaBr | NMP | 161 | 100 |
| 43 | Cu(10), Mn(10) | NaBr | TEG | 420 | 100 |
| 44 | Cu(10), Mn(10) | NaBr | PEG | 377 | 100 |
| 45 | Cu(10), Mn(10) | NaBr | SULF | 233 | 100 |
| 46 | Bi(20), Eu(20) | NaBr | NMP | 270 | 146 |
| 47 | Bi(20), Eu(20) | NaBr | TEG | 333 | 146 |
| 48 | Bi(20), Eu(20) | NaBr | PEG | 304 | 146 |
| 49 | Bi(20), Eu(20) | NaBr | SULF | 289 | 146 |
| 50 | Bi(20), Eu(20) | NaBr | ACN | 365 | 146 |
| 51 | Ce(10), Zn(50) | TBAB | NMP | 253 | 179 |
| 52 | Ce(10), Zn(50) | TBAB | TEG | 259 | 179 |
| 53 | Ce(10), Zn(50) | TBAB | PEG | 222 | 179 |

Based on the above results, the benefit of using cosolvents in these particular catalyst combinations is apparent.

It will be understood that each of the elements described above, or two or more together, may also find utility in applications differing from the types described herein. While the invention has been illustrated and described as embodied in a catalyst composition and method for producing diaryl carbonates using bisphosphines, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A catalyst composition comprising the following and any reaction products thereof:
   (A) a Group VIII metal having an atomic number of at least 44 or a compound thereof,
   (B) at least one bromide or chloride salt,
   (C) at least one organic bisphosphine, and
   (D) at least one halophenoxide.

2. The composition of claim 1, wherein component B is at least one bromide salt.

3. The composition of claim 2, wherein component C has the formula $$(R^1)_2P\text{-}R^2\text{-}P(R^1)_2, \quad (I)$$

wherein each $R^1$ is independently a monovalent organic radical and $R^2$ is a divalent organic radical.

4. The composition of claim 3, wherein each $R^1$ is an aromatic or alicyclic radical.

5. The composition of claim 4, wherein each $R^1$ is phenyl.

6. The composition of claim 5, wherein $R^2$ is a $C_{3-8}$ aliphatic radical.

7. The composition of claim 1, wherein the Group VIII metal in component A is palladium.

8. The composition of claim 7, wherein component A is palladium(II) acetate or palladium(II) 2,4-pentanedionate.

9. The composition of claim 1, wherein component D comprises lead(II) oxide, a lead(II) aryloxide or lead(II) 2,4-pentanedionate.

10. The composition of claim 1, wherein compound D comprises a lead bromophenoxide.

11. The composition of claim 1, wherein component B is sodium bromide.

12. The composition of claim 1, wherein component B is a tetraalkylammonium bromide.

13. The composition of claim 1, further comprising (E) a cosolvent which is a polar organic liquid.

14. The composition of claim 13, wherein component E is an ether, amide, sulfone or nitrile.

15. A catalyst composition comprising the following and any reaction products thereof:
   (A) palladium or a compound thereof,
   (B) at least one of sodium bromide and a tetraalkylammonium bromide,
   (C) at least one of 1,3-bis(diphenylphosphino)propane and 1,4-bis(diphenylphosphino)butane and
   (D) at least one lead bromophenoxide.

16. A catalyst composition comprising the following and any reaction products thereof:
   (A) a Group VIII metal having an atomic number of at least 44 or a compound thereof,
   (B) at least one bromide or chloride salt,
   (C) at least one organic bisphosphine, and
   (D) at least one cocatalyst that is a compound of a metal other than a Group VIII metal having an atomic number of at least 44, wherein said cocatalyst comprises a salt of at least one of titanium, zinc, bismuth, europium, and lead.

17. The composition of claim 16, wherein component B is at least one bromide salt.

18. The composition of claim 17, wherein component C has the formula $$(I) \quad (R^1)_2P\text{-}R^2\text{-}P(R^1)_2,$$

wherein each $R^1$ is independently a monovalent organic radical and $R^2$ is a divalent organic radical.

19. The composition of claim 18, wherein each $R^1$ is an aromatic or alicyclic radical.

20. The composition of claim 19, wherein each $R^1$ is phenyl.

21. The composition of claim 20, wherein $R^2$ is a $C_{3-8}$ aliphatic radical.

22. The composition of claim 16, wherein the Group VIII metal in component A is palladium.

23. The composition of claim 22, wherein component A is palladium(II) acetate or palladium(II) 2,4-pentanedionate.

24. The composition of claim 16, wherein component D comprises lead(II)oxide, a lead(II) aryloxide or lead(II) 2,4-pentanedionate.

25. The composition of claim 16, wherein component B is sodium bromide.

26. The composition of claim 16, wherein component B is a tetraalkylammonium bromide.

27. The composition of claim 16, further comprising (E) a cosolvent which is a polar organic liquid.

28. The composition of claim 27, wherein component E is an ether, amide, sulfone or nitrile.

* * * * *